United States Patent
Sheperak (10) Patent No.: US 12,356,535 B2
(45) Date of Patent: Jul. 8, 2025

(54) PLASMA DIRECTED ELECTRON BEAM PRODUCTION OF NITRIC OXIDE

(71) Applicant: Thomas J. Sheperak, Swanton, OH (US)

(72) Inventor: Thomas J. Sheperak, Swanton, OH (US)

(73) Assignee: PLASMA FUTURES, LLC, Trevose, PA (US)

( * ) Notice: Subject to any disclaimer, the term of this patent is extended or adjusted under 35 U.S.C. 154(b) by 279 days.

(21) Appl. No.: 16/272,416

(22) Filed: Feb. 11, 2019

(65) Prior Publication Data

US 2020/0029415 A1    Jan. 23, 2020

Related U.S. Application Data

(60) Provisional application No. 62/629,929, filed on Feb. 13, 2018.

(51) Int. Cl.
*H05H 1/36*    (2006.01)
*H05H 1/46*    (2006.01)

(52) U.S. Cl.
CPC .............. *H05H 1/36* (2013.01); *H05H 1/46* (2013.01); *H05H 1/4622* (2021.05)

(58) Field of Classification Search
CPC .......... H05H 1/36; H05H 1/46; H05H 1/4622; H05H 1/38; H05H 1/42; H05H 1/44; H05H 1/2443; H05H 1/245; A61B 18/14; A61B 18/18; A61B 18/04
USPC ........................................ 219/121.36–121.55
See application file for complete search history.

(56) References Cited

U.S. PATENT DOCUMENTS

| | | | | |
|---|---|---|---|---|
| 9,750,120 | B2 * | 8/2017 | Lacoste ............... | C23C 14/3471 |
| 9,993,282 | B2 * | 6/2018 | Sheperak ................. | A61N 5/10 |
| 2014/0074090 | A1 * | 3/2014 | Lam ..................... | A61B 18/042 |
| | | | | 606/49 |
| 2014/0276201 | A1 * | 9/2014 | Woloszko .......... | A61B 5/14546 |
| | | | | 600/562 |
| 2014/0303549 | A1 | 10/2014 | Sheperak | |

(Continued)

OTHER PUBLICATIONS

N.A. "Will the radio wave welder beat the laser torch?", New Scientist, 1977, vol. 74, No. 1046, Retrieve from Internet: URL: https://books.google.nl/books?id=H7OkzcSOGLgC&pg=PA21&lpg=PA21&dq=radio+wave+welder+new+scientist&source=bl&ots=AbG-5sZ6m1&sig=ACfU3U2bYIvvD2f-YJZEY0Yq09uZ0VbyDA&hl=en&sa=X&ved=2ahUKEwiP7u6Ex6f2AhVR-6QKHfpDCXoQ6AF6BAgCEAM#v=onepage&q&f=false.

(Continued)

*Primary Examiner* — Vy T Nguyen
(74) *Attorney, Agent, or Firm* — Weisun Rao; Jun Chen; Venture Partner, LLC (57) ABSTRACT

A coaxial energy delivery system comprised of a radio frequency power supply as the preferred source of power, electron accelerator system, and electrically conductive tube to be fitted to permit the flow of a gas intended to be energized as a plasma, a point of discharge of the said gas, whether in tubular or columnar form, coincident with the point of emission of the electromagnetic wave, the emission of said electromagnetic wave at said point, utilization of a fraction of the potential energy at that point to form a plasma in such gas flow which plasma forms a conduit or waveguide to insulate and confine the electromagnetic wave in its interior, which is manifested as a visible beam in appearance and thereby directing such coherent electromagnetic wave to a target material to be coupled with such material and impart its energy thereto.

19 Claims, 8 Drawing Sheets

(56) References Cited

U.S. PATENT DOCUMENTS

2016/0251240 A1* 9/2016 Fraser ................. C02F 1/008
                                                        204/664
2017/0258119 A1* 9/2017 Ribbon ................ A61L 9/015

OTHER PUBLICATIONS

Jones et al. In: Carcass Disposal: A Comprehensive Review:, Non-Traditional & Novel Technologies, 2004, Retrieved from Internet: URL: https://citeseerx.ist.psu.edu/viewdoc/download?doi=10.1.1.128.2662&rep=rep1&type=pdf.

The Extended European Search Report, Application No. 19754054.5, dated Mar. 15, 2022.

* cited by examiner

200 "beams" emitted via 25" copper pipe containing 200 apertures.

PLASMA DIRECTED ELECTRON BEAM PRODUCTION OF NITRIC OXIDE

BACKGROUND OF THE INVENTION

This invention relates in general to a method and apparatus for a plasma directed electron beam production of nitric oxide.

SUMMARY OF THE INVENTION

Various aspects of this invention will become apparent to those skilled in the art from the following detailed description of the preferred embodiment, when read in light of the accompanying drawings.

BRIEF DESCRIPTION OF THE DRAWINGS

FIG. 4 depicts the components of the dissociating device, showing the reaction chamber, the dissociation/recombination zone, the conductive tube that serves as the FIG. 5 illustrates a Plasma Directed Electron Beam (PDEB) system that is in accordance with the present invention.

DETAILED DESCRIPTION OF THE PREFERRED EMBODIMENT

Described herein is a Coaxial Energy Delivery System utilizing the insulating properties of plasma as a waveguide to confine and direct a coherent electromagnetic wave of electrical energy at Radio Frequency, as the preferred embodiment, and utilizing the super conductive properties of plasma to provide a conductive path for the delivery of said electromagnetic wave to a target material. This can be described as plasma on the outside and beam on the inside, the plasma and the electromagnetic wave travelling coaxially from the point of emission to a target material and, as such, describing a Plasma Directed Electron Beam. This system effectively and efficiently dissociates atmospheric air and creates Nitric Oxide gas.

Figure 1:
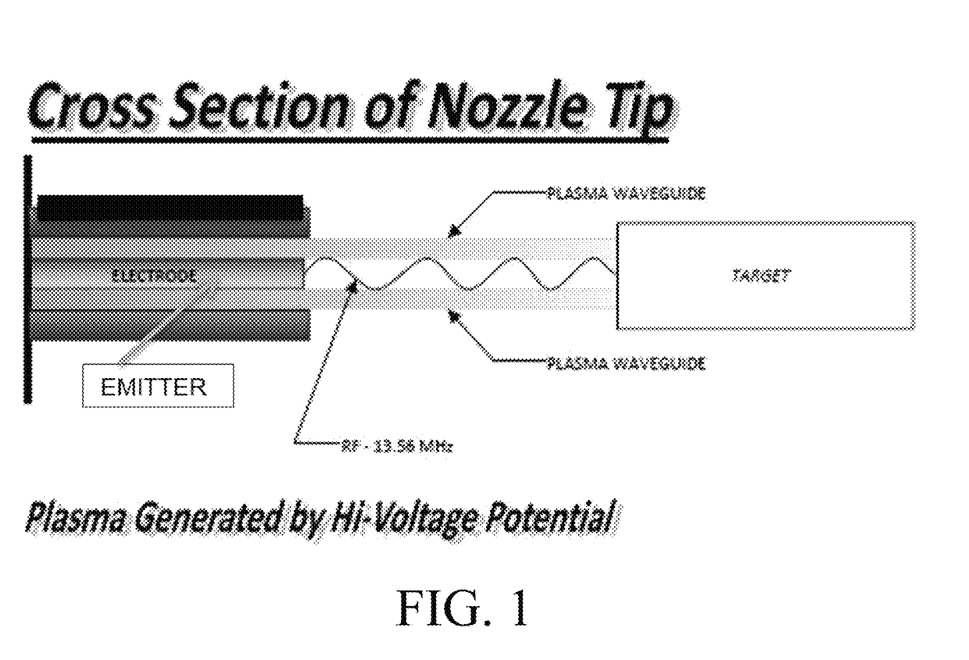
FIG. 1 is a depicts the cross section of the preferred embodiment for an emitter, showing the emitter coaxially surrounded by a plasma column, the plasma column insulating and containing the compressed electromagnetic wave and directing the wave to a target material.

FIG. 1 is a depicts the cross section of the preferred embodiment for an emitter, showing the emitter coaxially surrounded by a plasma column the plasma column insulating and containing the compressed electromagnetic wave and directing the wave to a target material.

Figure 2:
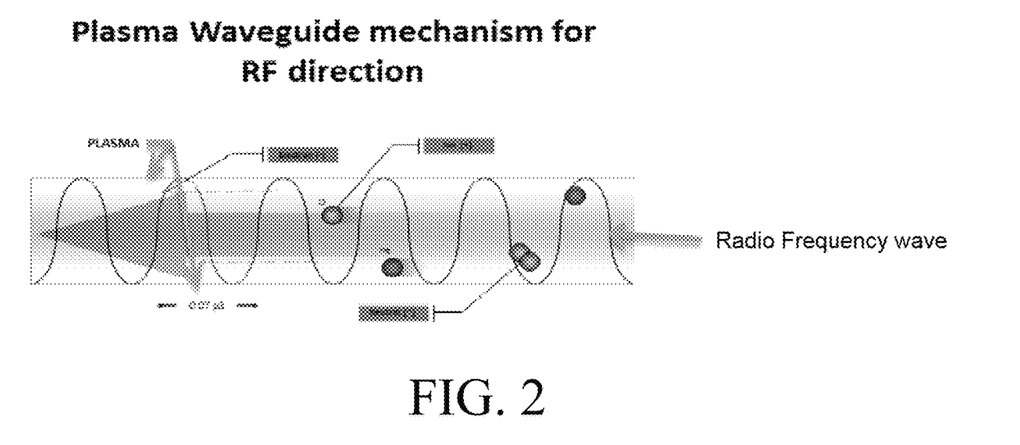
FIG. 2 depicts the energized state of the gas in plasma state and the sine wave representing the confined, coherent electromagnetic wave being directed to a target material.

FIG. 2 depicts the energized state of the gas in plasma state and the sine wave representing the confined, coherent electromagnetic wave being directed to a target material.

Figure 3:
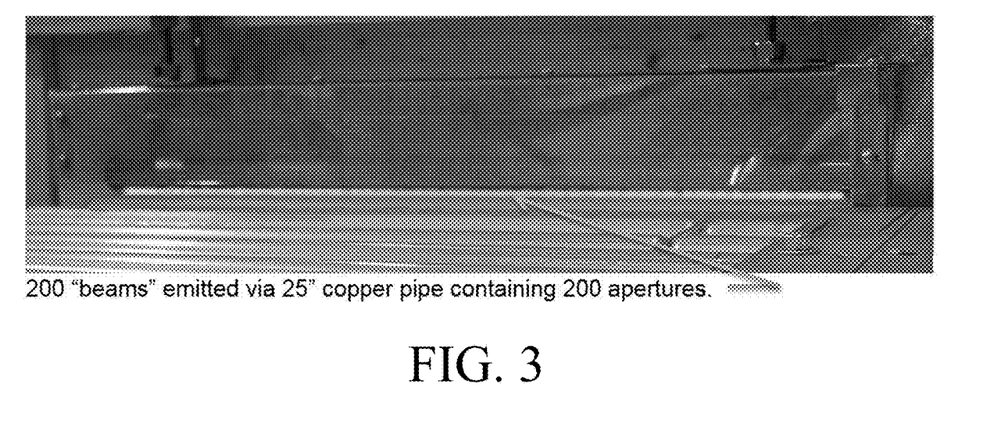
FIG. 3 depicts the "time-sharing" of the potential energy available at the virtual high voltage peak on a sine wave embodied within the coaxial insulator and depicts the generation of 200 beams emanating from the 200 apertures contained in 25 inch long copper pipe fabricated as described herein.

FIG. 3 depicts the "time-sharing" of the potential energy available at the virtual high voltage peak on a sine wave embodied within the coaxial insulator and depicts the generation of 200 beams emanating from the 200 apertures contained in 25 inch long copper pipe fabricated as described herein.

Figure 4:
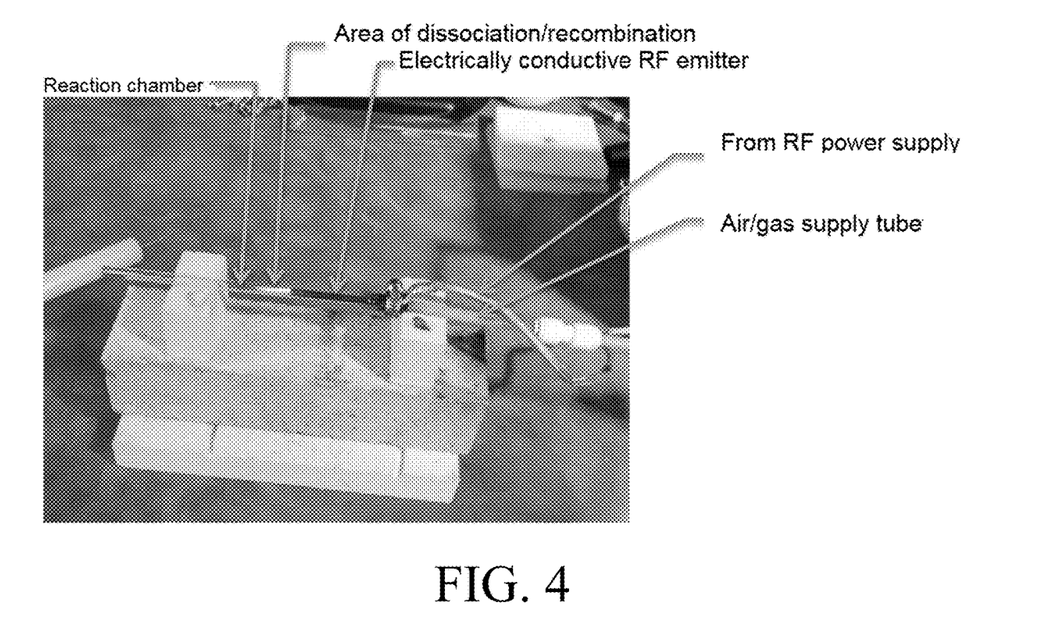

FIG. 4 depicts the components of the dissociating device, showing the reaction chamber, the dissociation/recombination zone, the conductive tube that serves as the radio frequency emitter, the electrical supply conductor from the RF power source and the air/gas supply tubing.

By manipulating the magnetic component of an electromagnetic wave, the electrons from a power source are accelerated to the point wherein the electrons, as a compressed wave, are spontaneously emitted from a metallic conductor surrounded by a tubular or columnar flow of a gas, such as Helium, Argon, atmospheric air and others. The electrons are accelerated to sufficient speed to energize the tubular or columnar flow of gas to the plasma state which, using the radio frequency insulating properties of plasma, confines and directs the electromagnetic wave, as a visible beam, coaxially, to a target material some distance away from the emitter. Neither the emission of the wave nor coupling of the wave to a target material requires a physical ground path return.

The relationship between the coaxial flow of the electromagnetic wave and the tubular or columnar flow of the gas energized to plasma state is symbiotic. The flow of gas depends upon the electromagnetic wave as its energy source to reach the plasma state and the electromagnetic wave depends upon the plasma for its travel linearly to reach a target to which this electromagnetic wave energy is delivered. Therefore, the electromagnetic wave energy creates its own conduit or waveguide as it propagates along its axis, coaxially with the plasma column.

Paradoxically, the outside portion of the plasma column serves as an insulator to confine and compress the electromagnetic wave, at radio frequency; and, on the inside, the plasma column serves as a super conductor to direct the electromagnetic wave to a target material. An example of a plasma serving as an insulator to radio frequency can be seen each time a returning spacecraft re-enters the atmosphere. The heat of friction caused by re-entry of the spacecraft causes the surrounding atmosphere to be ionized, creating a plasma. During the time the spacecraft is surrounded by this plasma, there is a radio blackout, meaning that the radio communications to and from the spacecraft are blocked. The technology described herein utilizes that radio frequency insulating property to create the waveguide to confine and direct the electromagnetic radio wave.

We are familiar with the knowledge that radio frequency energy travels from a radio station broadcast antenna as an ever expanding sphere. This technology miniaturizes that antenna, surrounds it with a column of gas and creates a waveguide that prevents the radio frequency from expanding as a sphere. The compressed radio frequency can now be directed with high energy density from the RF emitter to point to a target material which can be a liquid, a solid or a gas. We now have directed energy—electricity traveling through the air without a metal conductor, in a controlled manner.

The electromagnetic wave delivered to a target in this coaxial system is at such a frequency so as to resonate either at the primary or at a harmonic frequency thereof, thereby elevating the electrons of such material to a higher energy state which, among other things, results in the emission of photons. This causes the target materials to more easily and efficiently melt, vaporize, dissociate or otherwise be modified, depending upon the desired outcome. This coaxial energy delivery system provides a reliable means to electrochemically manipulate and alter matter.

Examples of such manipulation include, but are not limited to:

The production of Nitric Oxide from the dissociation of $N_2$ and $O_2$ contained in atmospheric air which is 78% Nitrogen and 21% Oxygen and the recombination of the monatomic Oxygen and monatomic Nitrogen as Nitric Oxide gas in the predominantly Nitrogen enriched atmosphere for medical and non-medical uses.

Air is the feedstock for the production of NO. Since air is difficult to ionize, we have three methods to start the plasma utilizing air. They are the brief introduction of Helium to start the ionization of air, mechanical starter using a conductive rod or wire to briefly touch the emitter and the use of a Piezo device to provide a spark to start the ionization.

The present rate of NO generation is about 0.5 cubic feet per hour (14 liters/hour). The system is scalable to higher and lower rates.

For the bench testing, we used an Industrial Scientific gas detector, model Mx6 with sensors for NO at 0-1000 ppm and $NO_2$ at 0-150 ppm. During the generation of NO, the detector registered 1000 ppm and "over limit" readings for NO and 0.0 ppm for $NO_2$. The incident power supplied from the RF generator was set at 130 Watts for the feedstock flow rate and the size of the reaction chamber.

Air is roughly 1 part Oxygen ($O_2$) and 4 parts Nitrogen ($N_2$). It takes 9.76 eV to dissociate $N_2$ and 5.11 eV to dissociate $O_2$. This technology provides a consistent energy level to dissociate the $N_2$ which is higher than the energy level required to dissociate $O_2$. Both atomic N and atomic O are highly reactive and recombine as NO. This is confirmed by the absence of $NO_2$ (a hazardous gas) in the exiting gas stream. Based on this information, all (1 part air) of the Oxygen and 1 of the 4 parts of Nitrogen were used to form NO, leaving 3 parts of free Nitrogen. This indicates a high concentration of NO.

The preferred embodiment utilizes a quartz tube as the reaction chamber. Other chemically non-reactive materials can be used, such as fused silica and mullite, to name two such materials. The RF emitter is an electrically conductive hollow tube, closed at one end to facilitate the entry of the feedstock, which is air, and which is made of Tungsten as the preferred embodiment. The other end of said tube is open to permit the feedstock to enter the reaction chamber. Other conductive, chemically non-reactive materials may be used. The Radio Frequency is provided at 13.56 MHz as the preferred frequency, although other frequencies can be used.

The Nitric Oxide produced can be utilized as it exits the reaction chamber or it can be compressed and stored for later use.

The coaxial energy delivery system is scalable and is not limited to a single point of energy emission. Given the high potential energy available, as is represented on a sine wave representing the energy field, the high potential can be time-shared over a large area. Given the linear propagation of the electromagnetic wave, the linear path represented by the sine wave has a measurable length along which additional energy emitters can be can be fabricated to provide gas flow needed to form a columnar plasma at a point of electrical discharge, each of which emitter will cause a visible beam, each being comprised of plasma on the outside and beam (electromagnetic wave) on the inside. The means to create each additional beams can be as simple as drilling numerous holes in an electrically conductive tube, sealed at one end and with fittings provided at the other end to allow for the introduction of a flow of gas to be used to form the plasma waveguide. The conductive tube can be a length of several feet or there can be several tubes of shorter lengths with such holes and which tubes can be placed such as to form any geometric pattern to suit coverage of the coaxial energy delivery systems for an intended use.

Conventional or traditional plasma generating devices utilizing an arc, inductive coupling, capacitive discharge and the like, focus only on creating a plasma and rely only on the plasma to, itself, to do work, utilizing the free electrons of the plasma only. In such systems the number of free electrons is inconsistent. In each of these systems, the flow of gas as the feedstock for the plasma, is introduced to flow perpendicular to the energy source. For example, in an arc plasma system, utilizing two electrodes, the gas flows across the arc and the energy within the arc is imparted to the gas, providing energy to create a plasma state in the gas. The energy density contained in the plasma is reduced proportionately to the distance a cross section of the plasma travels away from the arc.

Additionally, an arc is a violent occurrence, electrically, causing degradation and wear on the electrode materials. This necessitates periodic replacement of the electrodes along with related maintenance.

In inductively coupled plasma systems, the energized coil used to impart energy to the gas to be energized to plasma state surrounds, for a given distance, an electrically conductive or non-conductive tube running along the central axis of the coil. The energy from the coil follows a path perpendicular to the gas flow. In the case of using an electrically conductive tube containing the flow of a gas, the inductively coupled power would be extended by the conductive tube to the gas exit end of such tube, the plasma would still lose its energy proportionately as the distance of a cross section of such plasma increases from the tip of that tube, the source of its energy. In addition, the coil providing the induced energy to the flowing gas radiates 360 degrees, meaning that only a portion of the available radiated energy is applied to the flowing gas and the remainder is wasted by radiating such energy to the ambient. This is wasted energy requiring higher operating power.

These traditional devices rely solely on plasma to do work, which is only one of the two components provided by the coaxial energy delivery system described herein. In contrast to conventional plasma generating systems, the coaxial energy delivery system described herein utilizes plasma as the material to create a conduit or waveguide for the electromagnetic wave which wave is the integral component of the energy directly imparted to the target work material, not just the plasma. This results in very efficient use of the energy, considering that about 95% of the electromagnetic wave energy available is directly conveyed to and imparted in the target work material. This results in requiring lower power consumption and energy cost savings. Additionally, the emission of the electromagnetic wave energy eliminates an arc, thereby eliminating the need for periodic electrode replacement and provides for maintenance free operation, improving reliability and low operating costs.

The coaxial energy delivery system can operate using alternative wave forms from a power generator, including but not limited to square wave, saw tooth wave, pulsed direct current, direct current or other wave forms.

The primary frequency, being radio frequency as the preferred embodiment herein, can be used as a carrier wave onto which an additional frequency or additional frequencies can be added. These additional frequencies would be the primary or a harmonic to the resonating frequency of the target material.

This technology is a platform technology that enables adaptation of its components to a wide variety of uses which benefit from this directed energy technology. Some uses are:

1. The production of Nitric Oxide from the dissociation of $N_2$ and $O_2$ contained in atmospheric air which is 78% Nitrogen and 21% Oxygen and the recombination of the monatomic Oxygen and monatomic Nitrogen as Nitric Oxide gas in the predominantly Nitrogen enriched atmosphere for medical and non-medical uses.
2. The production of free Hydrogen and nanoscale free Carbon particles by dissociating Methane ($CH_4$) and other hydrocarbon materials.
3. Vaporizing solid, liquid and gaseous materials for deposition of coating materials
4. Modifying the surfaces of materials by raising surface energy to improve bonding of coatings on such materials and improve bonding together of those materials.
5. Reversing the charge on Carbon particles to cause the homogenous separation of Carbon nanomaterials for uniform disbursement of such particles onto substrate materials.
6. Reversing the charge on powdered coal to provide more surface area on the coal particles for complete combustion of coal.
7. Providing the economical use of electric power for melting and vaporizing materials as exemplified by sublimating Tungsten at 3422° C. (6192° F.) by applying only 400 Watts of power through this Plasma Directed Electron Beam.
8. Destruction and desiccation of Prokaryotic organisms (Pathogens) for the sterilization of surfaces, including mammalian cells at surgical sites, without harm to the mammalian cells.
9. The acceleration of wound healing by stimulating blood flow to the wound site and by stimulating fibroblasts which release collagen, among other things, to accelerate such wound healing.
10. The acceleration of tendon, ligament and other soft tissue healing through the topical introduction of Nitric Oxide gas to the wound area.
11. The destruction of pathogenic organisms in the human oral cavity that cause periodontal and other oral diseases, without harm to the mammalian cells.
12. Heating atmospheric air for the purpose of drying grains.
13. Purifying water by destroying pathogens and neutralizing the toxicity of hazardous materials in water.
14. Destroying pathogens in and reducing the volume of human and animal sewage in sewage treatment.
15. Destroying medical waste.
16. Pyrolyzing municipal waste to recover methane.

The principle and mode of operation of this invention have been explained and illustrated in its preferred embodiment. However, it must be understood that this invention may be practiced otherwise than as specifically explained and illustrated without departing from its spirit or scope.

This invention relates in general to plasma generating devices and in particular to the use of a hybrid plasma device for treatment of skin wounds.

Some prior art plasma devices generally operate at relatively high voltage and current levels. As a result, such prior art devices may well damage skin as an attempt is made to use one to treat a wound surface. In some cases, prior art plasma devices generate Ultra violet wavelengths which also may damage skin. Additionally, prior art plasma devices utilize an arc or induction to ionize a gas which requires complicated configurations, close tolerances and component wear. Accordingly, a low power, single electrode and simple plasma device that could be adapted for wound treatment would be desirable.

The present invention relates to a plasma generating device that uses a unique means to create a cold, non-thermal plasma to enhance healing of wounds and skin surface abnormalities, and to kill pathogens on skin surfaces in humans and animals. The invention utilizes a cold plasma to contain and direct a stream of electrons and photons to such wounds, abnormalities and pathogens and contemplates a portable hand-held apparatus to accomplish those purposes. The invention also contemplates a method for the use of such system and apparatus to accomplish those purposes.

The present invention contemplates a system that includes an electrode for establishing a shaped plasma for directing an electron beam. A gas supply is connected to the electrode to support the plasma. The system also includes a voltage supply connected to the electrode for energization of the plasma and establishment of the electron beam.

The present invention also contemplates a method for treating wounds that includes providing the system described above and then energizing the electrode to establish a Plasma Directed Electron Beam (PDEB) and to create a supply of photons that are guided within the plasma. The PDEB is then directed toward a wound.

Various objects and advantages of this invention will become apparent to those skilled in the art from the following detailed description of the preferred embodiment, when read in light of the accompanying drawings.

Figure 5:
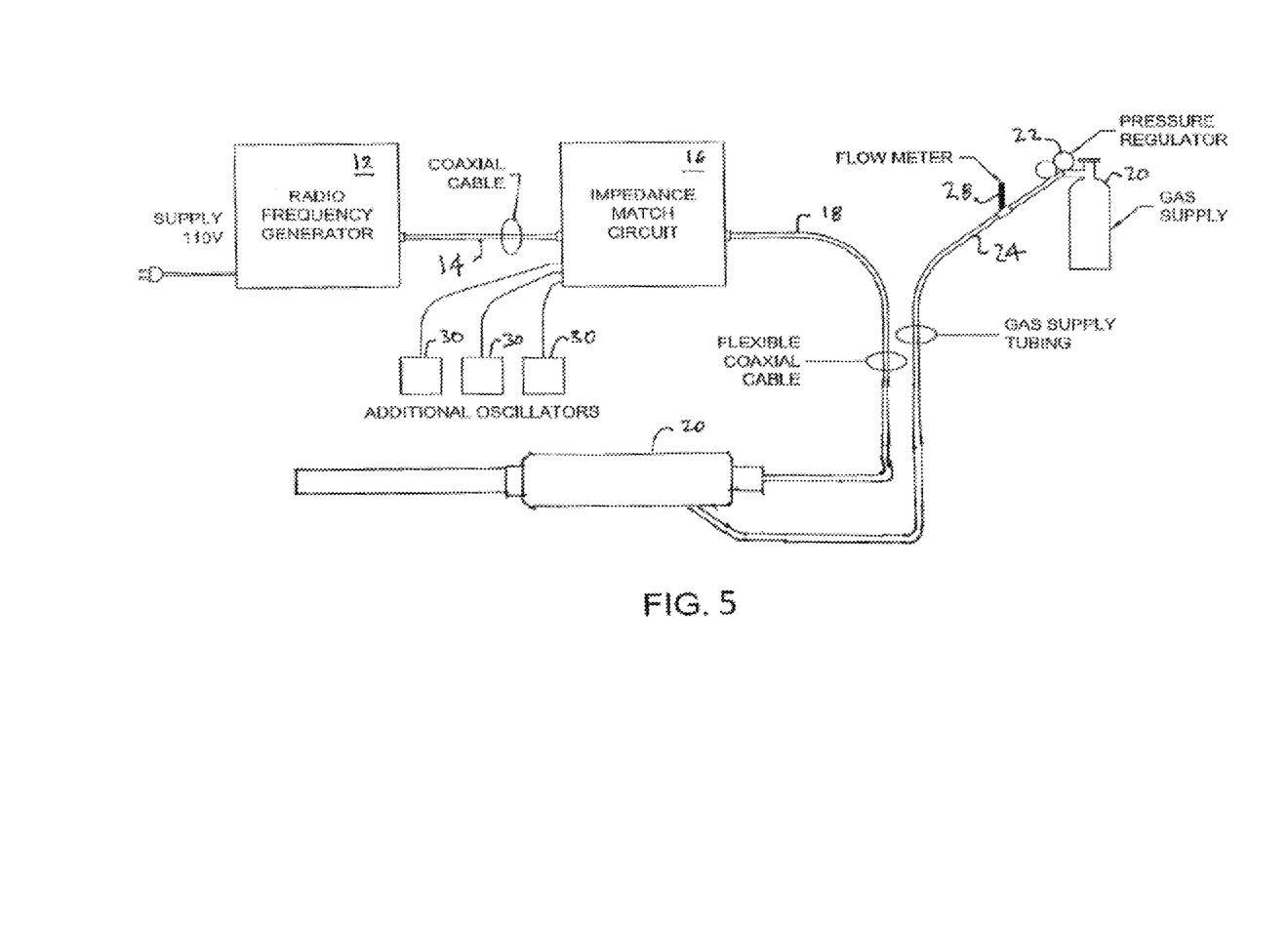

FIG. 5 illustrates a Plasma Directed Electron Beam (PDEB) system that is in accordance with the present invention.

Figure 6:
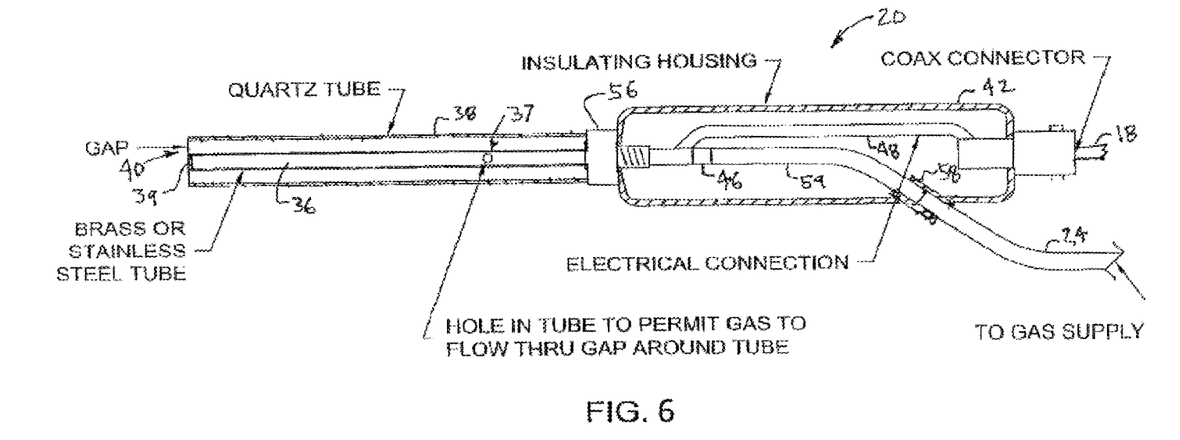
FIG. 6 is sectional view of a first embodiment of a PDEB generator that is included in the system shown in FIG. 5.

FIG. 6 is sectional view of a first embodiment of a PDEB generator that is included in the system shown in FIG. 5.

Figure 7:
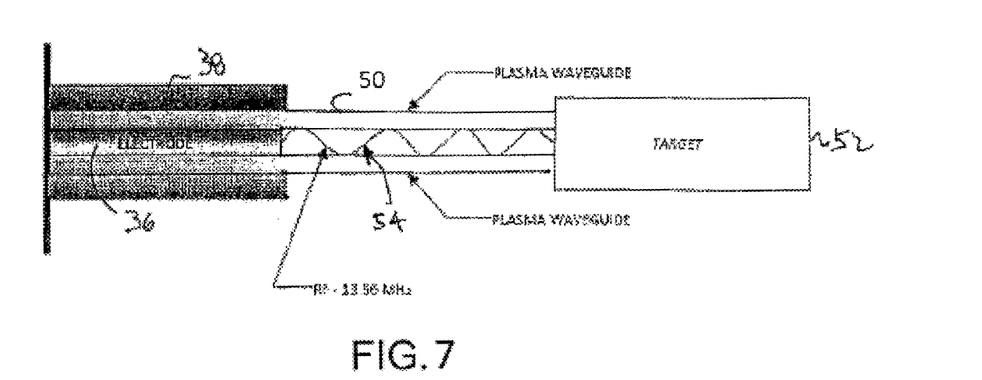
FIG. 7 illustrates the generation of a Plasma Directed Electron Beam by the system shown in FIG. 5.

FIG. 7 illustrates the generation of a Plasma Directed Electron Beam by the system shown in FIG. 5.

Figure 8:
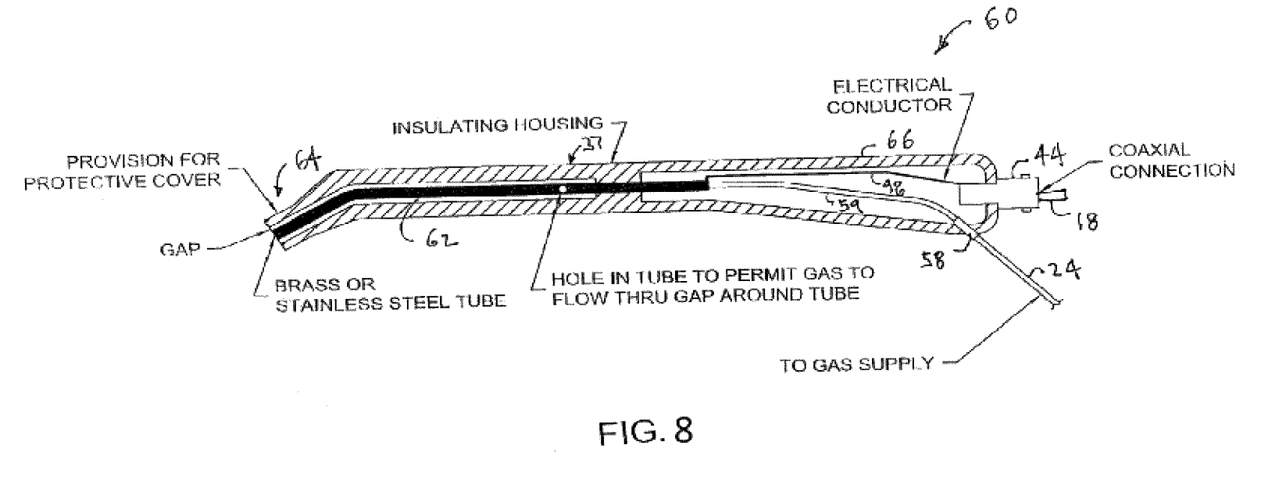
FIG. 8 is sectional view of a second embodiment of a PDEB generator that is included in the system shown in FIG. 5.

FIG. 8 is sectional view of a second embodiment of a PDEB generator that is included in the system shown in FIG. 5.

Figure 9:
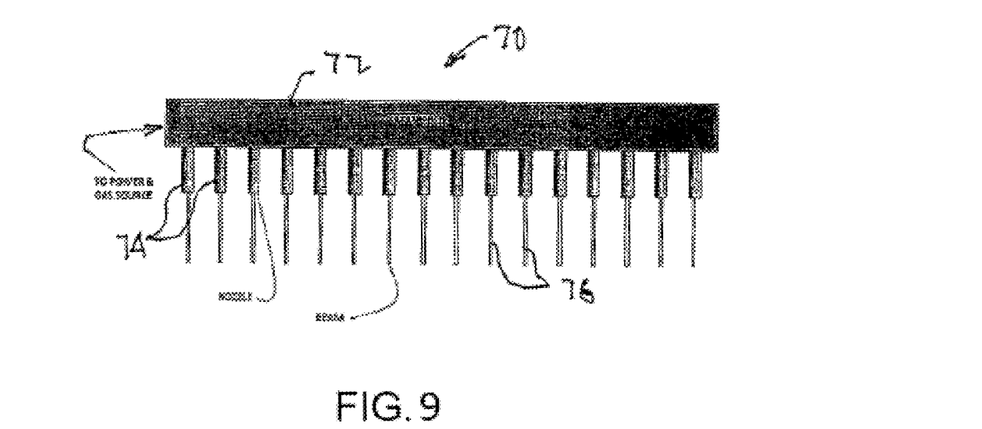
FIG. 9 illustrates another embodiment of the PDEB generator that may be included in the system shown in FIG. 5.

FIG. 9 illustrates another embodiment of the PDEB generator that may be included in the system shown in FIG. 5.

Figure 10:
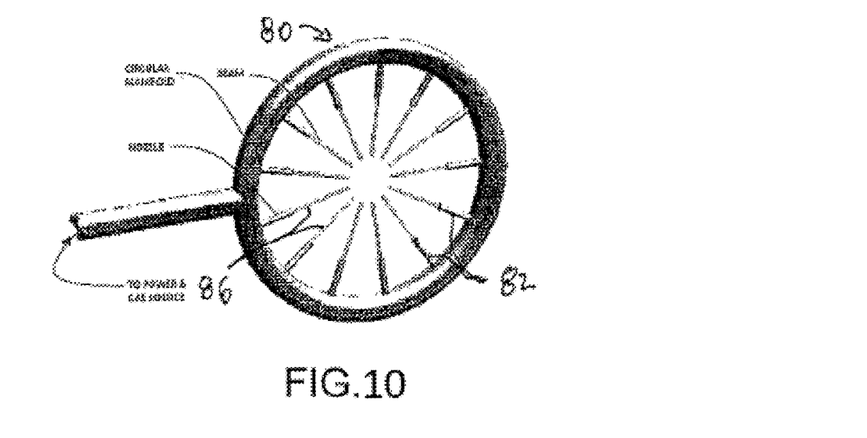
FIG. 10 illustrates another embodiment of the PDEB generator that may be included in the system shown in FIG. 5.

FIG. 10 illustrates another embodiment of the PDEB generator that may be included in the system shown in FIG. 5.

Figure 11:
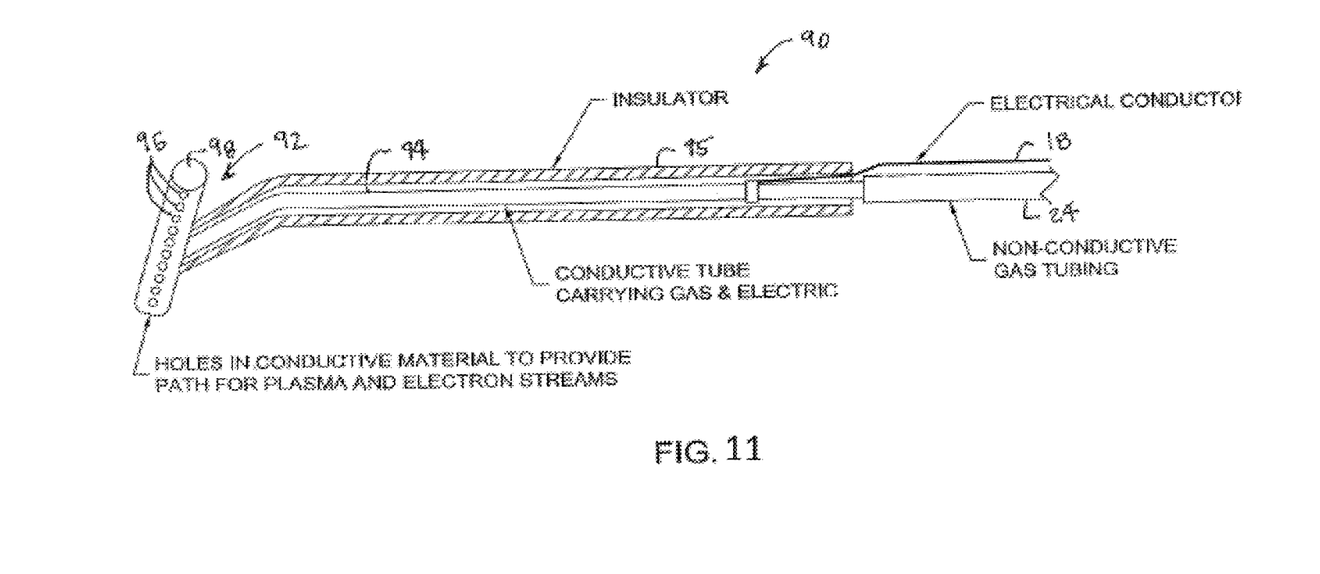
FIG. 11 illustrates another embodiment of the PDEB generator that may be included in the system shown in FIG. 5.

FIG. 11 illustrates another embodiment of the PDEB generator that may be included in the system shown in FIG. 5.

Figure 12:
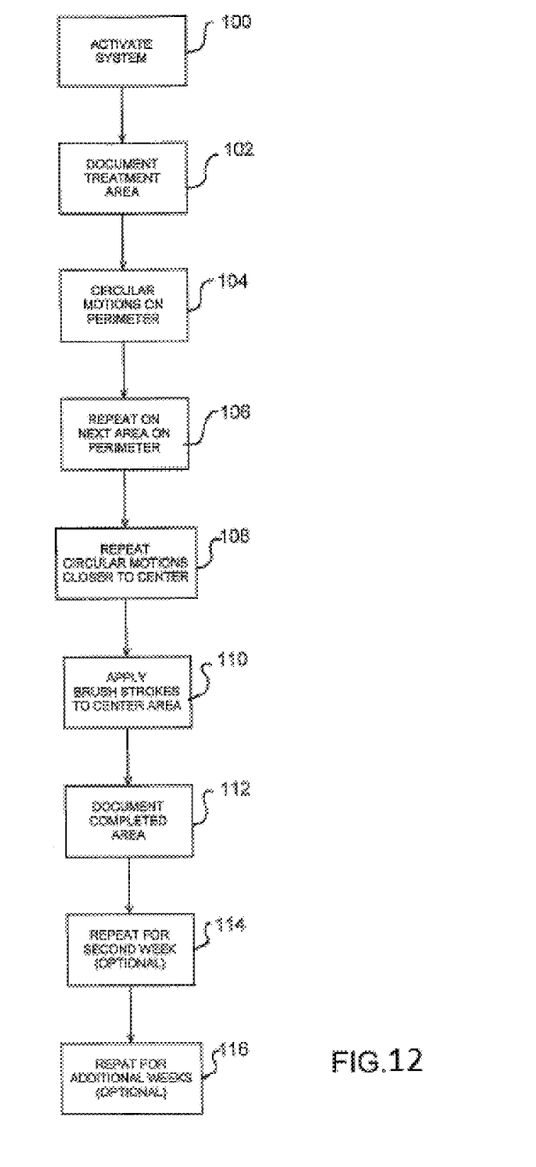
FIG. 12 is a flow chart for a method of operation for the PDEB system shown in FIG. 5.

FIG. 12 is a flow chart for a method of operation for the PDEB system shown in FIG. 5.

Unlike prior art plasma devices which energize (ionize) gases through arc or induction, the Plasma Directed Electron Beam (PDEB) system uses the electrical potential from a single electrode to generate sufficient plasma to serve as a waveguide sheath for the transmission of a coherent, non-axially propagating electromagnetic wave. The high energy density electromagnetic wave, coupled with the non-thermal plasma waveguide sheath, provide the singularly distinct advantages of this technology. Rather than relying on the chemical reaction caused by the ions and radicals in a plasma to change the chemical composition of the components of a wound, the PDEB dissociates certain materials to permit a safe recombination. Simply put, electricity travels through the plasma guide to provide the desired function.

The single electrode emission of a plasma guided coherent electromagnetic wave simplifies the configuration of the delivery device in contrast to the prior art plasma devices, eliminating the need for a critically aligned cathode and anode or geometrical accuracy for the induction circuitry. The present invention, and the accompanying improvements and discoveries create the ability to operate at power ranges between 5 Watts and 30 Watts with simplified circuitry, non-critical geometrical alignments and long component life. This invention produces a cold, non-thermal plasma to serve as the waveguide for a radio frequency beam that directs emitted electrons to the intended target, hence the name, Plasma Directed Electron Beam (PDEB). The benefits of this cold plasma waveguide are, among others, that the beam produced by the apparatus, when directed to the skin of a recipient, causes no discomfort, pain or burns, permitting the PDEB to pass across the wound area and healthy tissue without discomfort to the recipient or damage to healthy skin tissue.

The present invention utilizes a flexible cable attached between the output of the impedance matching circuitry and the hand held apparatus. Refined tuning procedures permit this lower power operation with micro-currents and permit the use of a flexible conductor which can extend a distance from the tuning network enabling the portability of the handheld wound care device.

Additionally, with the present invention, the radio frequency wave can be "time shared" in that the PDEB can be emitted from multiple apertures along a conductor and along parallel paths or a circular path, simultaneously, from a single conductor and single source of energy. This phenomena utilizes the properties of a linearly propagating wave form, in that the wave extends out from the source and back to the source, in this case, oscillating at 13.56 million times per second. When the conductor with multiple apertures is located at and along the virtual high voltage point of the wave (peak voltage), providing sufficient voltage to create a plasma and being approximately one meter in virtual length, each aperture, whether via a tubular electrode or just a hole in a hollow conductor, will produce the PDEB, simultaneously. This is accomplished with little additional power input for the reason that as the waveform extends outbound, the high voltage potential strikes a plasma and emits electrons at the closest aperture along the conductor, then continuing to move outbound, the voltage potential strikes a plasma and emits electrons at the next aperture, continuing outbound accomplishing the same striking a plasma and emitting electrons at each successive aperture location along the conductive path. This phenomenon is sequential and yet appears simultaneous at all apertures at once. In this instance the peak voltage on the waveform is on and off at 13.56 million times a second, a speed which the human eye cannot detect causing the appearance of all apertures operating at the same time.

Referring now to the drawings, there is illustrated in FIG. 5 a Plasma Directed Electron Beam (PDEB) system 10. The system 10 includes a radio frequency generator 12 connected by a coaxial cable 14 to the impedance matching circuitry box 16. A second coaxial cable 18 connects the impedance matching box 16 to a PDEB generator 20. The PDEB generator 20 is connected to an inert gas supply 22 by gas supply tubing 24. The gas supply includes a pressure regulator 26 to maintain a constant pressure for the gas being supplied to the PDEB generator 20. Additionally, a flow meter 28 may be included to monitor the gas usage. The system 10 may also include one of more additional oscillator units 30 to provide additional resonant frequencies to the apparatus; however, the inclusion of such additional oscillator units is optional.

A sectional view of the PDEB generator 20 is shown in FIG. 6. As shown in the figure, the PDEB generator 20 includes a hollow straight tube electrode 36 that may be fabricated from brass, stainless steel or a similar material. The electrode 36 is axially disposed within a cylindrical quartz tube 38. While a quartz tube is illustrated in FIG. 6, it will be appreciated that the invention also may be practiced with a tube formed from any other similar nonconductive material, such as, for example glass or plastic. One end of the electrode 36 that is contained within the generator 20 is connected to the gas supply tubing 24 while the other end is sealed by a cap 39. The straight tube electrode 36 has at least one aperture 37 formed through its surface to permit the flow of the introduced gas through both the tube electrode and the surrounding gap 40 formed between the electrode 36 and the quartz tube 38. The gas flows in a laminar manner to establish a waveguide. The electrode 36 and quartz tube 38 are mounted upon, and extend from, an insulated housing 42. The insulated housing also carries a coaxial connector 44 for attachment of the second coaxial cable 18 that carries the incoming radio frequency energy. A connector 46 is provided to connect the gas supply tube 24 to the open end of the electrode 36. Electrical connections 48 are disposed within the housing 42 to electrically connect the radio frequency energy to the electrode 36.

The inventor has successfully built and operated a PDEB system having the specific design features described in following paragraphs.

The housing 42, or shell, of the PDEB generator 20 is fabricated from an insulating material which should provide shielding to contain the RF energy or other electrical energy within the housing. The material must be dense enough to prohibit the infusion or growth of pathogens on the surface. The nozzle/electrode configuration were formed from $3/32$ inch brass tubing 36 as the electrode and surrounded by with quartz tubing 38. The electrode is approximately 2 inch long. A preferred inside diameter for the quartz tubing 38 is $1/8$ inch with a $1/32$ inch annular gap around the electrode 36 to confine and direct the gas in a laminar flow. Generally, the gap width should be about half of the diameter of the aperture formed in the electrode tubing; however, larger or smaller gaps may be utilized. The quartz tubing 38 is cut to be flush with the tip of the electrode 36. The electrode 36 is press fit into a hole drilled into the top of a large head 8-32 screw 56. The quartz tubing 38 is then centered around the brass electrode 36 and attached to the head of the screw 56 with an adhesive so as to provide an airtight seal. An aperture (not shown) hole is drilled into the side of the brass tubing electrode 36 at about $1/2$ inch from the point that tubing is press fit into the screw 56. The aperture provides for gas flow between the brass and quartz tubes. While one aperture was used in the prototype, it will be appreciated that the invention also may be practiced with a plurality of apertures formed through the brass tubing forming the electrode 36.

A coaxial cable 18 of adequate length is the preferable conductive media to convey the RF energy from the impedance matching circuit 16 to the hand held PDEB generator 20. As the present, a radio frequency of 13.56 MHz is used that represents a wavelength of about 20 meters. A coaxial cable length of two feet was arbitrarily utilized; however, given that the high voltage peak on a 20 meter wave can easily be about 1 meter, the coaxial cable may also be approximately one meter long. The length of the coaxial cable will affect the tuning in the impedance matching circuit 16. Coaxial cable mimics capacitance; therefore, compensating inductance and capacitance must be adjusted accordingly, either manually and/or automatically. The coaxial cable may be connected to the PDEB generator 20 by means of a coaxial connector 44 mounted upon the receiving end of the PDEB generator housing 42. A BNC connector was used in the prototype.

A conductive path is provided within the housing 42 for the radio frequency energy to flow from the source (impedance matching box) to the tip of the electrode. For the prototype, an insulated high voltage wire was soldered to a coax connector 57 on one end and to the electrode on the other; however, other commercially available methods may be used. With high voltage wire, RF shielding is provided inside the housing (not shown).

The source for the gas supply 22 is a standard tank of Helium, preferred at this time, although other gases and mixtures of gases will be used. The gas regulator 26 is set to provide a gas flow at 32 psi and the flow meter 28 is adjusted to provide flow rate between 5 to 10 standard cubic feet per hour. A connector formed from ⅛ inch Outside Diameter (OD) plastic tubing was utilized to connect the flow meter 28 to the hand held PDEB generator 20. A gas line connector 58 formed from a short section of ⅛ inch Inside Diameter (ID) tubing is mounted through the PDEB generator housing 42 and frictionally receives and retains the end of the ⅛ inch OD tubing. Within the housing 42, a length of ⅛ inch OD tubing 59 connects the brass tube electrode 36 to the inner end of the ⅛ inch OD connector 58.

Additional oscillators 30 are provided as needed for the particular application. While the invention contemplates that the RF generator 12 and any additional oscillators 30 generate sinusoidal time varying voltages, the invention also contemplates use of other power supplies such as, for example, pulsed DC, square wave, saw-tooth DC and 50 or 60 cycle AC. With regard to the additional oscillators, the invention contemplates that the RF generator 12 would supply a carrier frequency over which other frequencies are sent to the treatment surface. There are certain resonant frequencies which harm cells such as cancerous cells and other resonant frequencies that may be used to heal or strengthen cells. It is the intent of the present invention to overlay several of these frequencies, as needed, upon the 13.56 mHz carrier frequency. While prior art devices operated at higher voltages and currents, the present invention may be operated at 1,250 volts and 8 milliamps, a significant power reduction. The lower operating voltages and currents utilized with the present invention make possible the hand held device disclosed herein. Additionally, while 13.56 mHz is used in the description, frequencies in the range of 50 cycles to 900 mHz are contemplated for operation of the system 10 with 900 MHz being used for tissue ablation.

It will be understood that the prototype system 10 described above is intended to be exemplary and that the present invention may be practiced using different materials and dimensions from that which are described above.

As described above, electricity travels through the plasma guide to do the work, as illustrated in FIG. 7 where the operation of the PDEB generator 20 is illustrated. As shown in FIG. 7, a plasma sheath, or waveguide, 50 is generated and directed toward a target 52. The plasma sheath 50 contains and directs a coherent, non-axially propagating high energy electromagnetic wave 54. The plasma directed electron beam generated by the present invention differs from prior art plasma devices, generally, in that it serves to induce and maintain the high energy state of the surrounding and confining plasma it generates. This occurs irrespective of the distance the energized species travel away from the electrode and it further serves to excite the molecules of the surface materials to which it is directed. In traditional prior art plasma devices, the excitation takes place only at the discharge or excitation point of a plasma device and the energized species decay proportionally to the distance the plasma travels away from their discharge or excitation point.

An alternate embodiment 60 of the PDEB generator is illustrated in FIG. 8 where components that are similar to components shown if FIGS. 5 and 6 have the same numerical identifiers. In the alternated embodiment 60, an angled brass or stainless steel electrode 62 is utilized with provision for the placement of a disposable protective cover 64 at the electrode tip end. This sketch also shows the molding of the insulating housing 66 to provide a gap around the electrode 62, replacing the quartz tubing used on the PDEB generator 20 shown in FIG. 6. The angled electrode 62 provides a more comfortable means of holding the apparatus and effectively covering the treatment area. FIG. 8 also shows the gas and electrical connections which are substantially the same as shown in FIGS. 5 and 6.

Another alternate embodiment 70 is shown in FIG. 9 that includes a linear manifold 72 upon which are mounted a plurality of nozzles 74. The configuration generates multiple parallel plasma/energy beams 76 for creating a sterilizing pathway over a treatment area having a width of one half to four or more inches wide.

Yet another alternate embodiment 80 is shown in FIG. 12 that includes a circular manifold 82 upon which are mounted a plurality of inward facing nozzles 84. The configuration generates multiple converging plasma/energy beams 86 for creating a sterilizing pathway over a treatment area having a diameter of one half to four or more inches. In both of the embodiments 70 and 80, a manifold carrying a plurality of spaced apart nozzles is utilized to spread a number of beams over a wide area. The particular pattern may be changed by changing the shape of the manifold to provide different beam patterns, such as, for example, a diamond shape or elliptical shape (not shown).

While a tubular electrode or a tube within a tube may be desirable where precise application and direction of the PDEB is required, the present invention also contemplates using a simple hole in a hollow conductor (not shown), properly sealed to retain gases required, that emits a cold plasma directed electron beam and multiple such beams. A variation of this embodiment is shown at 90 in FIG. 11. The illustrated embodiment 90 includes a tubular T-shaped hand held nozzle 92. A section of ⅜ inch tubing 94 is disposed within a generally tubular insulator 95, The tubing 94 is connected to the base of the T and carries gas to the nozzle.

A plurality of apertures 96 are formed through the cross piece of the nozzle 92 and are operative to emit the plasma sheath and energy beam. End caps 98 seal the ends of the cross piece.

The method of operation of the system 10 will now be described in light of the flow chart shown in FIG. 12. In functional block 100, the system and the Helium or other inert or reactive gas supply is turned on. Upon beginning treatment, a photograph of the wound area is taken in functional block 104 and observations of the wound before treatment are noted. In functional block 104, the PDEB generator 20 is held much like a pencil or paintbrush and moved in a small circular motion, holding the tip of the PDEB generator about 2 millimeters from the surface of a wound. The initial motion is directed toward an area upon the outer perimeter of the wound area. The movement should be timed at about one revolution in one to two seconds, providing complete coverage of the first circular area on the wound.

After the first circle is completely exposed to the PDEB, the generator is moved to the next adjacent wound area in functional block 106 and the circular motion is repeated for one to two seconds. This pattern is duplicated until the entire perimeter area of the wound has been exposed to the PDEB with the area covered by each circular motion overlapping the area covered by previous circular motion.

Once the entire perimeter of the wound has been covered, in functional block 108, an area adjacent to the previously exposed area that is closer to the center of the wound is selected and the circular pattern of exposure is duplicated with a series of circular motions. The circular pattern with the circular motion of the apparatus is repeated until all areas surrounding the center of the wound have been exposed to the PDEB.

When the unexposed center of the wound area is approximately ¼" wide, the treatment advances to functional block 110 to begin a back and forth brushing motion with the apparatus starting at an edge of the unexposed wound area, brushing back and forth in a pattern to traverse the unexposed wound area until all of the remaining unexposed area has been exposed. Upon completion of the treatment, a second photograph of the wound area is taken in functional box 112 and after treatment observations of the wound are noted. The circular pattern and brushing pattern should be repeated every other day for the first week.

Exposure may be scheduled for every 3.sup.rd day during the second week, depending upon progress of healing, as shown in functional block 114. Exposure may be continued for two additional weeks as determined by the physician, as shown in functional block 116.

The present invention dissociates the toxins secreted by dead pathogens and thereby lessens the bio-load residual in a wound area while also creating excited species in the plasma waveguide including electrons, photons, radicals, ions and neutrals. Ultra violet spectrum photons generated by the present invention enhance the coagulation of the blood in a wound area.

The present invention can utilize a gas combination consisting of an inert gas such as, for example, Helium, and 2% Oxygen to generate Atomic Oxygen. The Atomic Oxygen is then utilized at the wound site to accelerate healing.

The present invention reveals a number of improvements over prior art plasma beam devices and applies the improvements to a use not heretofore contemplated. This use involves the acceleration of the healing of wounds in humans and animals and the sterilization of the wound surfaces, instantly killing all pathogens including bacteria, bacteria spores, fungi, molds, prions and viruses. The present invention has been demonstrated to remove and heal the situs of basil cell carcinoma (skin cancer), without surgery, within a period of 34 days, all without damage to surrounding and underlying healthy cells and tissue. The present invention has been demonstrated to dissociate volatile organic compounds associated with wound care procedures. The present invention has been demonstrated to sterilize surfaces ancillary to the wound care environment which include porous and non-porous surfaces as well as hard and soft surfaces such as Styrofoam with no damage to such surfaces.

In summary, the present invention provides the following features: Acceleration of the healing of wounds in humans and animals; Sterilization of the wound surfaces, instantly killing all pathogens including bacteria, bacteria spores, fungi, molds, prions and viruses.

Dissociation of volatile organic compounds associated with wound care procedures.

Sterilization of surfaces ancillary to the wound care environment which include porous and non-porous surfaces as well as hard and soft surfaces such as Styrofoam with no damage to such surfaces.

Operation at power ranges between 5 Watts and 30 Watts which produce a cold, non-thermal plasma to serve as the waveguide for the radio frequency beam providing the emission of electrons to the intended target;

Causes no discomfort, pain or burns, when the beam produced by the system is directed toward the skin of a recipient, permitting the PDEB to pass across the wound area and healthy tissue without discomfort to the recipient or damage to healthy skin tissue;

Provides refined impedance matching procedures to permit this lower power operation with micro-currents and permit the use of a flexible conductor which can extend a distance from the tuning network enabling the portability of the handheld wound care device;

Removes and heals the situs of basil cell carcinoma (skin cancer), without surgery;

Allows the radio frequency wave to be "time shared" so that the PDEB can be emitted from multiple apertures along a conductor and along parallel paths or a circular path, simultaneously, from a single conductor and single source of energy;

Does not need a nozzle or tubular electrode in all applications of the technology. While a tubular electrode or a tube within a tube may be desirable where precise application and direction of the PDEB is required, a simple hole in a hollow conductor, properly sealed to retain gases required, will emit a cold plasma directed electron beam and multiple such beams;

Lower operating voltages and currents make possible the hand held device disclosed herein;

nozzles and manifolds can be configured in various shapes and forms, extending the work distance of this technology over larger areas and over irregularly shaped areas permitting larger area coverage at a minimal addition of energy;

The plasma directed electron beam generated by the present invention differs from prior art plasma devices, generally, in that it serves to maintain the high energy state of the surrounding and confining plasma it generates for the entire length of the beam. This occurs irrespective of the distance the charged species travel away from the electrode and it further serves to excite the molecules of the surface materials to which it is directed;

The Plasma Directed Electron Beam (PDEB) uses the electrical potential from a single electrode to generate sufficient plasma to serve as a waveguide for the transmission of a coherent, non-axially propagating electromagnetic wave at these low power settings;

The Plasma Directed Electron Beam (PDEB) creates photons which are directed to a wound site and penetrate the epidural layer of tissue;

The excitation to plasma state of inert and reactive gases directed to a wound site;

The present invention contemplates a means to provide multiple beams to cover larger wound site areas;

The present invention contemplates a means to provide a manifold with multiple beams to sterilize surface areas;

The present invention also may be utilized to produce atomic oxygen directed and direct same to the situs of a wound; an apparatus that is hand held as described herein; a method to treat wounds and skin abnormalities as described herein any frequency can be used to generate the PDEB; wave forms other than radio frequency can generate the PDEB, including square waves, saw tooth waves, pulsed direct current and direct current or any other wave form; and additional oscillators can be connected to the system which would provide additional resonant frequencies to the output of the PDEB, using the 13.56 mHz wave as a carrier frequency.

While any frequency may be used to generate the PDEB, 13.56 mHz is selected because the Federal Communications Commission has designated it as one of the Industrial, Scientific and Medical frequencies to be used.

This plasma directed electron beam differs from plasma devices, generally, in that it serves to maintain the high energy state of the surrounding and confining plasma it generates, irrespective of the distance the charged species travel away from the electrode and it further serves to excite the molecules of the surface materials to which it is directed. In traditional plasma devices, the excitation takes place only at the discharge or excitation point of a plasma device and the energized species decay proportionally to the distance the plasma travels away from their discharge or excitation point.

In accordance with the provisions of the patent statutes, the principle and mode of operation of this invention have been explained and illustrated in its preferred embodiment. For example, the embodiment of the PDEB generator shown in FIG. 2 may be modified with the replacement of the quartz tube 38 by an molded insulated housing that extends over the electrode 36, as illustrated in FIG. 4. However, it must be understood that this invention may be practiced otherwise than as specifically explained and illustrated without departing from its spirit or scope.

What is claimed is:

1. A system for generating nitric oxide gas comprising:
a radio frequency power supply, an electron accelerator system, a gas supply, an electrically conductive tube connected to the radio frequency power supply and the gas supply, and a reaction chamber connected to the electrically conductive tube, said system being structured and configured such that:
a flow of a gas is generated, wherein the gas is supplied by the gas supply and introduced into the electrically conductive tube;
a point of discharge of the gas, whether in tubular or columnar form, is coincident with a point of emission of an electromagnetic wave emitted from the electrically conductive tube; and
a fraction of a potential energy at the point of emission is used to form a plasma in the flow of the gas such that the plasma forms a conduit or waveguide that insulates and confines the electromagnetic wave in an interior of the plasma, which is manifested as a visible beam in appearance, and thereby directs a coherent electromagnetic wave to the reaction chamber, wherein the reaction chamber has a length in the direction of the electromagnetic wave, thereby enabling the electromagnetic wave to cause a disassociation of the gas, and wherein disassociated elements are recombined to generate a high concentration of nitric oxide gas in the reaction chamber.

2. The system for generating nitric oxide gas of claim 1, wherein the radio frequency power supply provides any of a square wave, a saw tooth wave, a pulsed direct current, or a non-pulsed direct current.

3. The system for generating nitric oxide gas of claim 2, wherein insulating properties of the plasma are used to confine and direct the compressed electromagnetic wave, and wherein super conducting properties of the plasma are used to convey the coherent wave from the point of emission to the reaction chamber.

4. The system for generating nitric oxide gas of claim 1, wherein the electron accelerator system is configured to facilitate emission of the electromagnetic wave from the electrically conductive tube and formation of the plasma.

5. The system for generating nitric oxide gas of claim 1, wherein the radiofrequency power supply generates both a primary frequency and other frequencies that are compatible with a resonant frequency or frequencies of the target material.

6. The system for generating nitric oxide gas of claim 1, wherein the electrically conductive tube has at least one aperture, in the form of a hole or a hole with an additional electrically conductive tube attached to such hole, that facilitates the formation of the plasma conduit or waveguide on the outside and the electromagnetic wave on the inside.

7. The system for generating nitric oxide gas of claim 1, that is structured and configured to electro-chemically alter, manipulate, or otherwise change matter, including atoms or molecules.

8. The system for generating nitric oxide gas of claim 1, wherein the gas is atmospheric air, and the system is structured and configured to generate nitric oxide gas from the dissociation of atmospheric air and the recombination of monatomic oxygen and monatomic nitrogen as nitric oxide gas.

9. The system for generating nitric oxide gas of claim 8, wherein the electrically conductive tube discharges both the electromagnetic wave and the gas into the reaction chamber and thereby causes dissociation of the atmospheric air and recombination of the atomic nitrogen and atomic oxygen as nitric oxide.

10. A device for generating nitric oxide gas comprising:
an electrode for establishing a shaped plasma for directing an electron beam to a reaction chamber;
a gas supply connected to the electrode to introduce a gas to the electrode and support the plasma; and
a voltage supply connected to the electrode for energization of the plasma and establishment of the electron beam, wherein the device is structured and configured to generate nitric oxide gas, and wherein the reaction chamber has a length in the direction of the electron beam, thereby enabling the electron beam to cause a dissociation of the gas, and dissociated elements are recombined to generate a high concentration of nitric oxide gas in the reaction chamber.

11. The device of claim 10 wherein the voltage supply includes one of a radio frequency oscillator, a pulsed DC generator, a square wave generator, a saw-tooth generator, a 50 cycle AC generator, a 60 cycle generator, and a DC voltage supply.

12. The device of claim 11 further including an impedance matching circuit connected between the electrode and the voltage source.

13. The device of claim 12 wherein the impedance matching circuit includes at least one of an adjustable inductance and an adjustable capacitance.

14. The device of claim 13 wherein the adjustable component is manually adjustable.

15. The device of claim 13 wherein the adjustable component is automatically adjustable.

16. The device of claim 12 further including a nozzle, wherein the electrode is disposed within the nozzle.

17. The device of claim 16 wherein the electrode has at least one aperture extending therethrough for emission of gas into a gap defined between the electrode and an inner surface of the nozzle, the electrode and the nozzle being structured and configured to form a laminar gas flow that becomes a cold plasma for containing a flow of energy within the plasma.

18. The device of claim 17 further including a manifold, wherein the electrode is disposed within the manifold.

19. The device of claim 18 wherein a plurality of apertures extend through the manifold.

* * * * *